US005238548A

United States Patent [19]
van der Wal et al.

[11] Patent Number: 5,238,548
[45] Date of Patent: Aug. 24, 1993

[54] MEMBRANE SELECTIVE FOR METAL IONS

[75] Inventors: Peter D. van der Wal; Udo H. Verkerk, both of Enschede; Gerardus W. N. Honig; Hermanus A. J. Holterman, both of Hengelo; Jan R. Haak, Enschede; David N. Reinhoudt, Hengelo, all of Netherlands

[73] Assignee: Priva Agro Holding B.V., De Lier, Netherlands

[21] Appl. No.: 885,960

[22] Filed: May 18, 1992

[30] Foreign Application Priority Data

May 17, 1991 [NL] Netherlands ............... 9100872

[51] Int. Cl.$^5$ ............................. G01N 27/26
[52] U.S. Cl. .................... 204/418; 204/416; 204/296
[58] Field of Search ............. 204/416, 418, 296; 568/18, 20, 74, 77, 589, 36, 37, 39, 44, 45, 50, 56, 57

[56] References Cited

U.S. PATENT DOCUMENTS 4,214,968 7/1980 Battaglia et al. ............. 204/416

FOREIGN PATENT DOCUMENTS

0258951A2 of 1988 European Pat. Off. .
0262633A2 of 1988 European Pat. Off. .
2086925A of 1982 United Kingdom .

OTHER PUBLICATIONS

Sudhölter, E. J. R., et al., *Sensors and Actuators* 17:189-194, 1989.
Search Report issued by the Dutch Patent Office (Feb. 21, 1992) in the priority application (NL-91.00872).

Primary Examiner—John Niebling
Assistant Examiner—Bruce Bell
Attorney, Agent, or Firm—Christensen, O'Connor, Johnson & Kindness

[57] ABSTRACT

An ionophore according to the general formula I wherein the substituents are chosen such that the ionophore is either also polymerized in the matrix of a membrane selective for metal ions or interwoven therewith. Thus obtained is a membrane having a long useful life for use in diverse sensors such as ISFET, ion-selective electrode, and the like.

9 Claims, 1 Drawing Sheet

MEMBRANE SELECTIVE FOR METAL IONS

TECHNICAL FIELD

The invention relates to a membrane selective for metal ions, in particular a membrane that is selective for bivalent cations.

BACKGROUND OF THE INVENTION

Membranes selective for metal ions are used for example in ion-selective sensors which are used for measuring the concentration or activity of a certain ion type in an electrolyte solution. The operation is based on the occurrence of a potential difference across the membrane selective for metal ions that separates the test solution from a reference solution. Examples of such sensors are the ION Selective Field Effect Transistor (ISFET), electrode, optrode, coated-wire electrode, and sensors based on planar silicon technology.

For the present invention the ISFET is of particular importance. A number of membranes are arranged on the gate region of an ISFET. In addition to a hydrophilic membrane, the so-called hydrogel, there is a hydrophobic membrane. The electro-active components are included in the matrix of this latter membrane. On the one hand these are the ionic sites which determine the so-called perm-selectivity, that is, the selectivity for either anions or cations. On the other hand there is a selectivity-determining group which determines the selectivity of the membrane for a specific ion.

The selectivity-determining group included in a membrane matrix can for instance be an ion exchanger or a neutral ionophore. To indicate bivalent cations, ionophores which are based on diamides, in particular dioxaoctane diamides, are usually employed. In the development of such dioxaoctane diamides two properties are important, namely on the one hand the selectivity which determines which (bivalent) ion is bonded, and on the other the lipophilicity which determines the speed at which the ionophore is washed out of the membrane and thereby determines the useful life of the sensor.

The selectivity can be influenced using substituents which determine the relative position of the coordinating ligands O, S, and SO, or through the choice of the type of coordinating ligand: O, S, or SO.

With known dioxaoctane diamide derivatives the lipophilicity is often influenced by arranging long alkyl chains on the amide groups. Such long alkyl chains form as it were an anchoring in the membrane matrix which prevents washing out of the ionophore. It is assumed by some that arranging such long alkyl chains also influences the position of the coordinating ligands and thereby the selectivity.

SUMMARY OF THE INVENTION

It has now been found that the useful life of a sensor can be extended to a significant extent by use of ionophores according to the general formula:

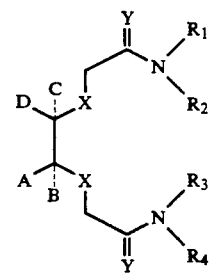

wherein:
X represents O, S, or SO;
Y represents S or O;
$R_1$, $R_2$, $R_3$, and $R_4$ represent $(C_1-C_5)$alkyl, polyether, an intramolecular or intermolecular $(C_1-C_{10})$alkyl bridge or polyether bridge;
at least A, B, C, or D is a group with the formula:

—$(CEF)_m$—G and the other A, B, C, and D are hydrogen $(C_1-C_5)$alkyl, $(C_5-C_7)$aryl, $(C_1-C_7)$aryl, halogen (selected from chlorine, bromine, fluorine, and iodine), or $(C_5-C_7)$aryl$(C_1-C_5)$alkyl, wherein:
$m \geq 0$;
E and F are equal or different and represent hydrogen, $(C_1-C_5)$alkyl, or and
G is a group for covalent bonding to the membrane;
or A, B, C, and D form a saturated $(C_5-C_7)$cycloalkyl group, which group is substituted by the group —$(CEF)_m$—G wherein $m \geq 0$;
or A, B, C, and D form an aromatic $(C_5-C_7)$aryl group which is substituted by the group —$(CEF)_m$—G wherein $m \geq 0$; wherein:
E and F are equal or different and represent hydrogen, $(C_1-C_5)$alkyl, or halogen; and
G is a group for covalent bonding to a membrane. G is preferably a group derived from hydroxyl, halogen, amine, amide, ketone, aldehyde, enamine, epoxide, carboxylic acid ester acylhalogen, acid anhydride, allylether ($CH_2=CH-CH_2-O-X$, wherein X can be any group), acryl, vinyl, methacryl, alkenyl, alkynyl, sulphide, sulphonic acid, sulphonic acid ester, silane, or siloxane.

Due to the modifiable group G which is arranged on the 3,6 dioxa-bridge and which can enter into a covalent bonding with the membrane, the washing out of the ionophore is prevented whereby the useful life of the sensor is significantly extended without essentially influencing the selectivity of the ionophore arranged in the membrane.

In addition, ionophores according to the general formula I can be used wherein:
X represents O, S, or SO;
Y represents S or O;
$R_1$, $R_2$, $R_3$, and $R_4$ represent $(C_1-C_5)$alkyl, polyether, an intramolecular or intermolecular $(C_1-C_{10})$alkyl bridge or polyether bridge;
at least A, B, C, or D is a group with the formula:

—$(CEF)_m$—G and the other A, B, C, and D are hydrogen, $(C_1-C_5)$alkyl, $(C_5-C_7)$aryl, $(C_1-C_5)$alkyl$(C_5-C_7)$aryl, halogen or $(C_5-C_7)$aryl$(C_1-C_5)$alkyl, wherein:

$m \geq 0$;

E and F are equal or different and represent hydrogen, ($C_1$-$C_5$)alkyl, or halogen; and G is a group covalently bonded with an oligomer Q;

or A, B, C, and D form a saturated ($C_5$-$C_7$)cycloalkyl group which is substituted by the compound —(CEF)$_m$—G—Q wherein $m \geq 0$;

or A, B, C, and D form an aromatic ($C_5$-$C_7$)aryl group which is substituted by the combination —(CEF)$_m$—G—Q in which $m \geq 0$;

wherein:

E and F are equal or different and represent hydrogen, ($C_1$-$C_5$)alkyl, or halogenide; and G is a group covalently bonded with an oligomer Q;

G is preferably a group derived from hydroxyl, halogenide, amine, amide, ketone, aldehyde, enamine, epoxide, carboxylic acid ester, acylhalogen, acid anhydride, allylether, acryl, methacryl, alkenyl, alkynyl, sulphide, sulphonic acid, or sulphonic acid ester. Q is an oligomer with a suitable molecular weight related to the membrane polymer. Q is preferably a hydrophobic oligomer having a length of preferably 5 or more monomer subunits, more preferably 10-80 monomer subunits, wherein the monomers can be olefins, urethanes, siloxanes, esters, amides, ethers, or combinations thereof. Representative examples include: a polysiloxane of about 30 monomer subunits; a dodecyl group. Q may be an intermolecular bridge between two or more ionophores or an intramolecular bridge in one ionophore.

During polymerization of the membrane the described ionophore is interwoven with the matrix whereby washing out the ionophore is prevented.

DETAILED DESCRIPTION OF THE PREFERRED EMBODIMENT

Compounds according to the present invention can be prepared without excluding other routes by protecting glycerol or a compound derived therefrom on the 1,2-position (R in the reaction diagram below) and in a following step by replacing the 3-OH group with the group (P in the diagram) for interweaving or covalent bonding with the matrix. After deprotecting the 1,2-position the ionophore is obtained after reaction with bromoacetamide.

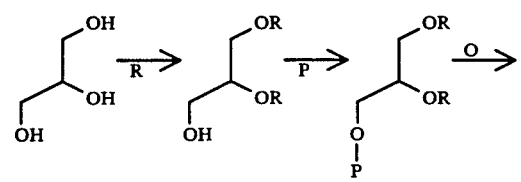

-continued

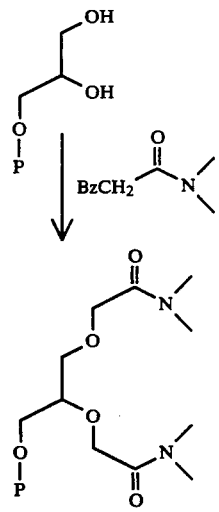

A characteristic example for the above preparation method is the etherization with allylalcohol of the 3-OH group from the commercially available Solketal TM, followed by a deprotection step. An ionophore that can be covalently coupled to the membrane matrix is then obtained by the reaction of the thus obtained glycerol derivative with bromoacetamide.

The present invention will be illustrated hereinbelow with reference to a number of examples which are not intended to limit the invention.

EXAMPLE 1 (comparison)

A solution consisting of 4% by weight photo-initiator, 2% by weight ionophore II (see table below), 94% by weight photopolymerizable siloxane, and 50 mol% (relative to ionophore II) potassium tetra(parachlorophenyl)borate in dichloromethane was arranged on an ISFET (modified as described 194 (1989); and U.S. Pat. No. 4,882,292, which is hereby incorporated by reference and after drying exposed for 2 minutes under UV light in a nitrogen atmosphere.

Figure 1A:
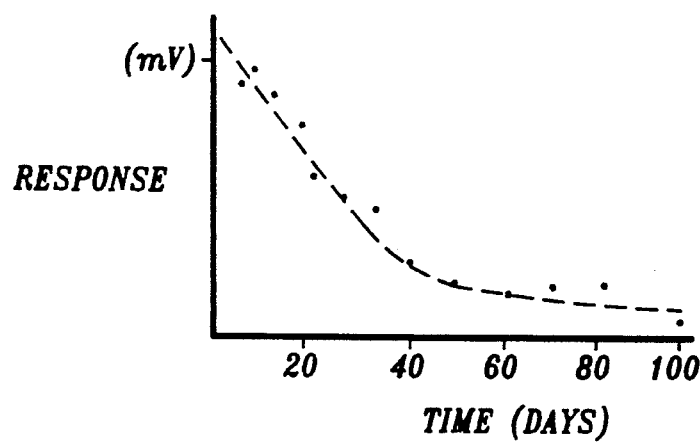
FIGS. 1A-C summarize the experimental results discussed in Examples 1-3, respectively.

The CHEMFETs (described generally in U.S. Pat. No. 4,882,292, at page 1, lines 59) formed in this way were held in continuous contact with the measurement solution. The response to calcium was found to diminish in the course of time, as shown in the graph of FIG. 1A.

EXAMPLE 2 (invention)

A solution consisting of 4% by weight photo-initiator, 2% by weight ionophore III (see table below), 94% by weight photopolymerizable polysiloxane, and 50 mol % (relative to ionophore III) potassium tetra(parachlorophenyl)borate in dichloromethane was arranged on a series of ISFETs (modified as described in Sudholter et al. Sensors and Actuators 17, 189-194 (1989); and U.S. Pat. No. 4,882,292) and after drying exposed for 2 minutes under UV light in a nitrogen atmosphere.

Figure 1B:
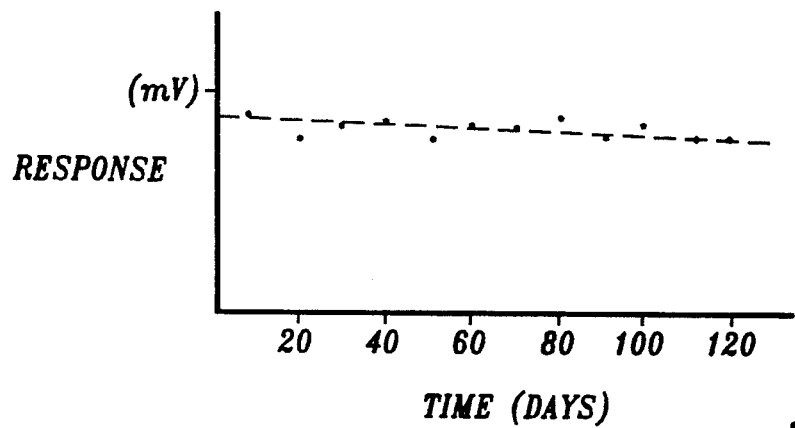

The thus formed MEMFETs were held in continuous contact with the measurement solution. The response to calcium diminishes very slowly, as shown in FIG. 1B. The FETs (Field Effect Transistors) have a longer useful life than the FETs of Example 1.

EXAMPLE 3 (invention)

A solution consisting of 4% by weight photo-initiator, 2% by weight ionophore IV (see table below), 94% by weight photopolymerizable polysiloxane, and 50 mol % (relative to ionophore IV) potassium tetra(parachlorophenyl)borate in dichloromethane was arranged on a series of ISFETs (modified as described in Sudholter et al., Sensors and Actuators 17, 189–194 (1989); and U.S. Pat. No. 4,882,292) and after drying exposed for 2 minutes under UV light in a nitrogen atmosphere.

Figure 1C:
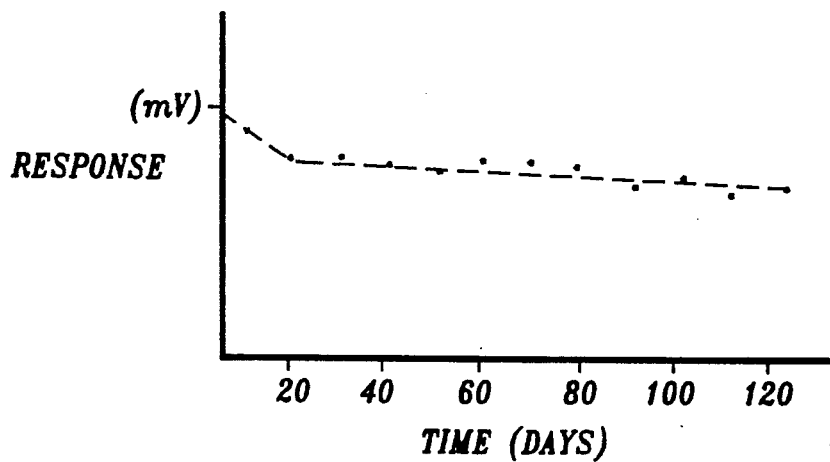

The thus formed MEMFETs were held in continuous contact with the measurement solution. The response to calcium only diminishes very slowly, as shown in FIG. 1C. The FETs have a longer useful life than the FETs of Example 1.

TABLE

Structure formulas of the ionophores from the Examples.

| ionophore | formulas |
| --- | --- |
| ionophore II | 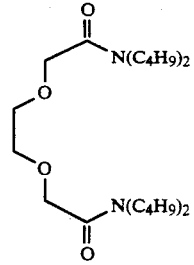 |
| ionophore III | 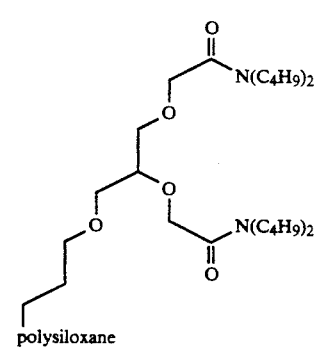 |
| ionophore IV | 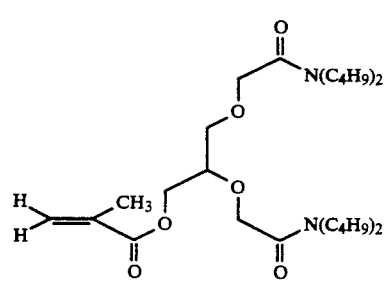 |

We claim:

1. Membrane selective for metal ions comprising an ionophore covalently bonded to the membrane with the general formula:

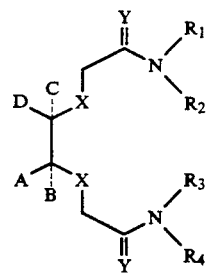

in which:
X represents O, S, or SO;
Y represents S or O;
$R_1$, $R_2$, $R_3$, and $R_4$ represent $(C_1-C_5)$alkyl, polyether, an intramolecular or intermolecular $(C_1-C_{10})$alkyl bridge or polyether bridge;
at least A, B, C, or D is a group with the formula:

—$(CEF)_m$—G and the other A, B, C, and D are hydrogen, $(C_1-C_5)$alkyl, $(C_5-C_7)$aryl, $(C_1-C_5)$alkyl$(C_5-C_7)$aryl, halogen or $(C_5-C_7)$aryl$(C_1-C_5)$alkyl, wherein:
$m \geq 0$;
E and F are equal or different and represent hydrogen, $(C_1-C_5)$alkyl, or halogen; and G is a group for covalent bonding to the membrane;
or A, B, C, and D form a saturated $(C_5-C_7)$cycloalkyl group, which group is substituted by the group —$(CEF)_m$—G, wherein $m \geq 0$;
or A, B, C, and D form an aromatic $(C_5-C_7)$aryl group which is substituted by the group —$(CEF)_m$—G, wherein $m \geq 0$;
wherein:
E and F are equal or different and represent hydrogen, $(C_1-C_5)$alkyl, or halogen; and
G is a group for covalent bonding to a membrane.

2. Membrane as claimed in claim 1, characterized in that the group G covalently bonded to the membrane is derived from: hydroxyl, halogenide, amine, amide, ketone, aldehyde, enamine, epoxide, carboxylic acid ester, acylhalogen, acid anhydride, allylether, acryl, methacryl, alkenyl, alkynyl, sulphide, sulphonic acid, sulphonic acid ester, silane, or siloxane.

3. Membrane selective for metal ions, comprising a polymer membrane and an ionophore included in the polymer membrane with the general formula I, wherein:
X represents O, S, or SO;
Y represents S or O;
$R_1$, $R_2$, $R_3$, and $R_4$ represent $(C_1-C_5)$alkyl, polyether, an intramolecular or intermolecular $(C_1-C_{10})$alkyl bridge or polyether bridge;
at least A, B, C, or D is a group with the formula:

—$(CEF)_m$—G and the other A, B, C, and D are hydrogen, $(C_1-C_5)$alkyl, $(C_5-C_7)$aryl, $(C_1-C_5)$alkyl$(C_5-C_7)$aryl, halogenide or $(C_5-C_7)$aryl$(C_1-C_5)$alkyl, wherein:
$m \geq 0$;
E and F are equal or different and represent hydrogen, $(C_1-C_5)$alkyl, or halogen; and
G is a group covalently bonded to an oligomer Q;

A, B, C, and D form a saturated ($C_5$-$C_7$)cycloalkyl group which is substituted by the combination —(CEF)$_m$—G—Q, wherein $m \geq 0$;

or A, B, C, and D form an aromatic ($C_5$-$C_7$)aryl group which is substituted by the combination —(CEF)$_m$—G—Q, wherein $m \geq 0$;

wherein:

E and F are equal or different and represent hydrogen, ($C_1$-$C_5$)alkyl, or halogen; and G is a group covalently bonded to an oligomer Q.

4. Membrane as claimed in claim 4, characterized in that G is a group derived from hydroxyl, halogenide, amine, amide, ketone, aldehyde, enamine, epoxide, carboxylic acid ester, acylhalogen, acid anhydride, alylether, acryl, methacryl, alkenyl, alkynyl, sulphide, sulphonic acid, or sulphonic acid ester.

5. Membrane as claimed in claim 3, characterized in that the oligomer Q is an oligomer of a suitable molecular weight related to the membrane polymer.

6. Membrane as claimed in claim 1, characterized in that the membrane polymer is prepared by photopolymerization.

7. Sensor having incorporated therein a membrane as claimed in claim 1.

8. Membrane as claimed in claim 3, characterized in that the membrane polymer is prepared by photopolymerization.

9. Sensor having incorporated therein a membrane as claimed in claim 3.

* * * * *

UNITED STATES PATENT AND TRADEMARK OFFICE
CERTIFICATE OF CORRECTION

PATENT NO. : 5,238,548
DATED : August 24, 1993
INVENTOR(S) : P. D. van der Wal et al.

It is certified that error appears in the above-indentified patent and that said Letters Patent is hereby corrected as shown below:

| COLUMN | LINE | |
|---|---|---|
| 1 | 19 | "ION" should read --Ion-- |
| 1 | 20 | after "(ISFET)," insert --ion-selective-- |
| 2 | 22 | "$(C_1-C_7)$aryl" should read --$(C_1-C_5)$alkyl $(C_5-C_7)$aryl-- |
| 2 | 29 | after "or" insert --halogen;-- |
| 3 | 15 | "halogenide;" should read --halogen;-- |
| 4 | 39 | after "described" insert --in Südholter et al., Sensors and Actuators 17, 189- -- |
| 4 | 40 & 41 | "refer-ence" should read --reference)-- |
| 4 | 44 | "lines 59" should read --line 59-- |
| 4 | 62 | after "calcium" insert --only-- |
| 6 | 61 | ";, halogenide" should read --, halogen,-- |
| Claim 3 | Line 13 | |
| 7 | 1 | before "A, B, C" insert --or-- |
| Claim 3 | Line 20 | |
| 7 | 14 | "halogenide," should read --halogen,-- |
| Claim 4 | Line 2 | |

Signed and Sealed this

Fifth Day of April, 1994

Attest:

BRUCE LEHMAN

Attesting Officer     Commissioner of Patents and Trademarks